United States Patent [19]
Samson et al.

[11] Patent Number: 5,198,287
[45] Date of Patent: Mar. 30, 1993

[54] INSECT REPELLENT TENT FABRIC

[75] Inventors: Richard D. Samson; James M. McKinney, both of North Augusta; John Russell, Graniteville, all of S.C.

[73] Assignee: Graniteville Company, Graniteville, S.C.

[21] Appl. No.: 678,061

[22] Filed: Apr. 1, 1991

[51] Int. Cl.$^5$ .............................................. B32B 7/00
[52] U.S. Cl. .................................... 428/248; 8/115.7; 8/182; 8/115.59; 135/115; 424/403; 428/252; 428/264; 428/265; 428/907
[58] Field of Search ................ 135/115; 424/403; 428/248, 252, 264, 265, 907; 8/115.7, 182, 115.59

[56] References Cited
U.S. PATENT DOCUMENTS

| | | | |
|---|---|---|---|
| 3,769,060 | 10/1973 | Ida et al. | 428/907 |
| 3,859,121 | 1/1975 | Yeadon | 428/907 |
| 3,995,034 | 11/1976 | Strobel | 514/159 |
| 4,594,286 | 6/1986 | McKinney | 428/252 |
| 4,765,982 | 8/1988 | Ronning et al. | 424/402 |
| 4,833,006 | 5/1989 | McKinney et al. | 428/257 |
| 5,089,298 | 2/1992 | McNally et al. | 427/322 |

OTHER PUBLICATIONS

*Chemical Abstracts* 68(23): 104113.

Primary Examiner—James C. Cannon
Attorney, Agent, or Firm—Clifton Ted Hunt

[57] ABSTRACT

A tent fabric with a water repellent and flame retardant coating that includes the insecticide permethrin with an effective life of more than six months.

5 Claims, 3 Drawing Sheets

INSECT REPELLENT TENT FABRIC

FIELD OF THE INVENTION

This invention relates to coated fabrics that are flame resistant and water repellent and are treated by the present invention to be insect repellent.

BACKGROUND OF THE INVENTION

It is known to coat fabric with protective coating systems containing water repellent chemicals and flame retardant chemicals to make the fabric suitable for use as military tenting in all climates of the world. See, for example, U.S. Pat. Nos. 4,594,286 and 4,833,006.

It is, of course, desirable in most climates that the tent fabric also be insect repellent. Insect repellents are known but their effective life of only a few days renders them unsuitable for use in a protective coating system for tent fabrics.

There is, therefore, a universal need for tent, tarpaulin, and shelter fabrics (collectively referred to herein as tent fabrics) which have a long term capability of repelling annoying and disease carrying insects.

Many insect repellents are effective when they are applied to the skin as a spray or lotion, but only for a few hours. The protection time is extended to as much as a week or ten days when repellents are applied to clothing, gloves and body nets for outdoor use. Insect repellents with such a short effective life are impractical for use in a coating for tent fabric.

The tent fabrics with which this invention is concerned are treated to be durably water repellent and flame retardant, and to have an appearance that is pleasing to the eye. In order that these properties be retained, it is necessary that the fabric be treated with insect repellents that are effective for their intended purpose without adversely affecting any other desired property of the fabric.

Several commonly known insecticides have been tried with the coating used for tent fabric. For example, a production trial has been made of water repellent and flame retardant tent fabric utilizing dimethyl pthtalate (DMP) as an insecticide. It did not compromise the flame retardant or water repellent properties of the tent fabric but its length of effectiveness was less than desired.

Benzil benzoate, while readily dispersed in typical fire retardant coatings, demonstrated an unsightly appearance upon application and drying. Dibutyl phthalate and dibutyl adipate showed this to a much lesser extent.

Permethrin is a synthetic pyrethroid which exhibits repellent as well as knockdown and kill activity against insects. Pyrethroids, including both the naturally occurring compounds and their synthetically prepared analogs effectively control a variety of pests, such as houseflies, mosquitoes, cockroaches, etc. They are not harmful to plants, food, animals and humans, and leave no harmful residues. Permethrin is environmentally safe and has been found to be compatible with coating compositions containing water repellent chemicals and flame retardant chemicals, used for tent fabric, without adversely affecting the desired properties of the coated fabric.

Despite these highly favorable characteristics, permethrin has had only limited general utility because of its relatively short-lived insecticidal activity. This is due to its decomposition into a non-active, non-insecticidal product in the presence of oxygen and ultraviolet light. The speed of this decomposition is dependent upon the environment in which the permethrin is placed, but typically takes place in from several hours to several days or weeks. This instability of permethrin severely limits its usefulness as an insecticide.

Prior attempts to stabilize pyrethroids against degradation have included encapsulation and the addition of antioxidants and photostable ultraviolet light absorbent compounds to solutions of pyrethroids. Encapsulation has not been effective because the pyrethroids degrade almost as quickly inside the capsules as they do unencapsulated. Only moderate success in reducing degradation has been obtained by the addition of antioxidants and photostable ultraviolet light absorbent compounds to solutions of pyrethroids. Their moderate success is largely off-set by unsightly residues which are hard to remove.

Various techniques have been suggested for providing sustained release of a pyrethroid as an insect control agent. For example, U.S. Pat. No. 4,056,610 to Barber discloses a microcapsule insecticide composition in which a pyrethroid permeates a porous shell wall and maintains an effective level of the pyrethroid upon the outer surface of the shell wall to control insects for up to four days (then considered an extended length of time within the art). Control is achieved by killing insects which contact the pyrethroid released through the capsule wall.

U.S. Pat. No. 4,765,982 to Ronning discloses an insect control device comprising a plurality of rough surfaced cellulosic fibers wherein there is self-adhered to the surface of the fibers a liquid insecticide composition microencapsulated in a capsule whose shell is permeable to the liquid insecticide. The microencapsulated insect control agents disclosed in U.S. Pat. No. 4,056,610 to Barber are named as the preferred insecticide for use in Ronning's invention.

Ronning's insecticide-treated-rough-surfaced cellulosic fibers are formed into webs, tapes, sheets, pads, and various other relatively flat shapes suitable for use in particular locations, such as a ribbon-like tape for placement along the base of a building or door.

Ronning teaches that smooth-surfaced fibers do not act as good sites for adhesion of microencapsulated insect control agents. Ronning's rough surfaced cellulosic fibers treated with an insecticide are not suitable for a tent fabric. The texture of the rough surfaced fibers is not satisfactory and they are neither water repellent or flame retardant.

SUMMARY OF THE INVENTION

It is the primary object of this invention to provide a tent fabric with insect repellent properties that are effective for six months, or longer, without compromising the water repellence, flame retardance, or other desirable properties of the tent fabric, thereby offering maximum convenience and safety to the user.

DETAILED DESCRIPTION OF THE INVENTION

The substrate of the insect repellent tent fabric of this invention may be any suitable fabric. For example, it may be a plain weave polyester fabric or a 50/50 blend of polyester and cotton, woven as an oxford fabric. The invention has been practiced satisfactorily with a substrate made from continuous multifilament yarns with normal producer's twist of one or two turns per inch and woven into a plain weave fabric containing 84 yarns per inch in the warp and 32 yarns per inch in the weft.

The fabric is coated with a composition which renders it water repellent, flame retardant, and insect repellent. The following composition is exemplary of coatings that can be used to practice the invention:

EXAMPLE 1

Insect Repellent Coating for Tent Fabric

| COMPONENT | PERCENTAGE | FUNCTION |
| --- | --- | --- |
| Emkay B.C. | 0.45 | Defoamer |
| Polyvinyl Chloride Polymer (Geon 576) | 18.37 | Binder |
| Dioctyl Phthalate | 5.99 | Plasticizer |
| Sodium Salt of Phosphated Ester | 0.25 | Surfactant |
| Antimony Trioxide | 13.83 | Flame Retardant |
| Kaolin (Hydrated Aluminum Silicate) | 19.20 | Flame Retardant |
| Methylated Melamine Formaldehyde Resin | 1.72 | Cross-linker |
| Methylcellulose | 0.27 | Thickener |
| Bromochlorinated Hydrocarbon | 27.66 | Flame Retardant |
| Zirconium Wax Complex | 1.51 | Water Repellent |
| Pigment Systems | 1.79 | Color |
| Acrylic Copolymer (Acrysol ASE-60) | 0.98 | Thickener |
| Metasol TK-100 Powder | 0.15 | Mildew Inhibitor |
| Permethrin | 07.83 | Pesticide |
|  | 100.00% |  |

Permethrin is an immobile material but can be made mobile with a plasticizer. In addition to serving as a water repellent in the normal coating for tent fabric, the zirconium wax complex also serves as a plasticizer and as a protector against oxygen for the permethrin. The wax creates a shell around the permethrin that protects the permethrin from degradation by oxygen after the permethrin reaches the surface of the coating. The wax also mobilizes the permethrin to the extent of keeping enough permethrin on the inner surface of the coating to be an effective insect repellent for a much longer period of time than has heretofore been possible.

As protection against environmental degradation such as ultra violet rays, the permethrin is not combined with the coating to be on the outside of the tent but is only combined with the coating applied to the side of the fabric which will be inside the tent. The wax and plasticizer, which provides mobility to the permethrin, is combined with the permethrin in the coating for the inside of the tent. Zirconium wax complex is also included as a water repellent in the coating for the outside of the tent.

Figure 1:
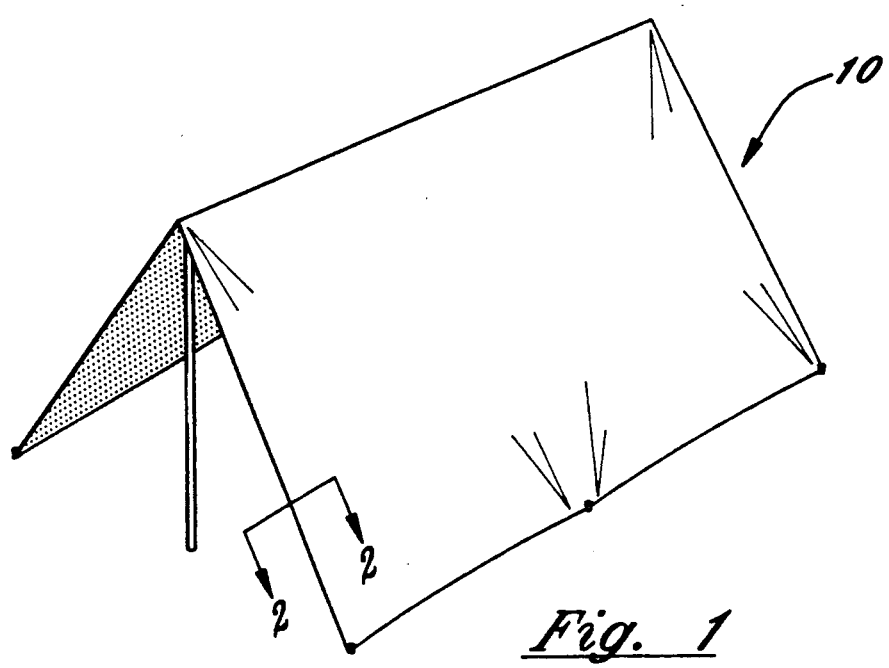
FIG. 1 is a perspective view of a tent.
Figure 2:
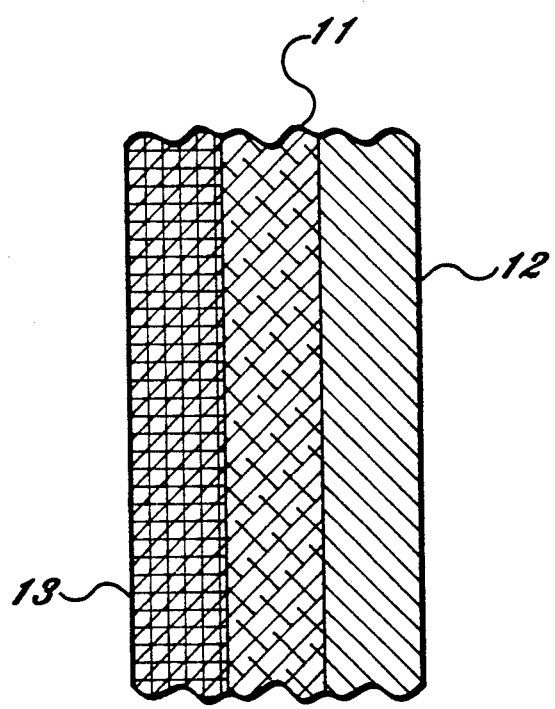
FIG. 2 is a sectional view taken substantially along the line 2—2 in FIG. 1.

Thus, as illustrated in FIGS. 1 and 2, insect repellent coating 13 for a water repellent and flame retardant tent 10 is applied only to the side of substrate 11 that will be inside the tent and a conventional water repellent and flame retardant coating 12 is applied to the side of the substrate 11 that will be outside the tent.

It is preferred that the coating on the outside of the tent be the coating described and claimed in U.S. Pat. No. 4,833,006 issued May 23, 1989 to Graniteville Company of Graniteville, S.C. The disclosure of that patent is incorporated herein by reference.

The effectivness of permethrin as an insect repellent in the coating for tent fabric has been field tested for a year by the Agricultural Research Service of the United States Department of Agriculture. They were evaluated using *Aedes aegypti* mosquitoes to determine which treatment would most effectively prevent bites and cause the most knockdown (KD) of the insects entering the tents.

Specifically, tests were conducted to determine the persistence of compounds applied to tents to keep out or kill mosquitoes. Three tents were used in the test. Each tent (family tent type) was constructed from 24.4 square meters of 100% textured polyester fabric having a weather resistant vinyl coating and a nylon screen-zippered door opening. One tent was treated with the permethrin-containing coating of Example 1, herein (inside only, including the floor); the second tent was treated with dimethyl phthalate (DMP) inside and outside the tent; and the third tent was untreated, to be used as a control.

The three tents were erected Oct. 30, 1989, at the USDA Medical & Veterinary Entomology Research Laboratory, Gainesville, Fla., in an open grassy field, two meters apart in a north-south row, each with its doorway facing east. They remained for one year, unshaded and fully exposed to the effects of weathering.

Efficacy assessments were made with weekly bioassays. Through the screen door zipper opening of each tent were released from 75 to 80 seven-day-old laboratory reared susceptible strain female *Aedes aegypti* mosquitoes. Upon release, the screen door was zipped closed, and the tent flaps and rear screen-covered window were left open for ventilation (tent flaps were kept closed at all other times). Mosquitoes were free to land or fly about inside the tent for three hours. Each hour after release, mosquito KD, i.e., mosquitoes dead or moving but unable to fly, and bite counts were recorded. Bites were observed and recorded after a one minute exposure of a volunteer's arm in the tent through a small opening unzipped in the screen door.

Hourly data indicated the rapidity of treatment effect on the mosquitoes during a three hour exposure, i.e., whether treatment effect was rapid (during the first hour) or additive (after two to three hours). The data also helped show when treatments began to lose potency because of exposure to weathering.

After three hours, mosquitoes were removed from each tent with a battery powered aspirator and counted. Care was taken to avoid contamination between treatments by entering the untreated, DMP-treated, and permethrin-treated tents in that order. Test data were recorded in terms of percent effect, i.e., number KD/biting divided by the total number of mosquitoes in the tent equals the percent KD/biting.

An attempt was made to keep the tests on a same-day schedule each week. Inclement weather at times made this difficult. However, forty eight of fifty two weeks of tests were completed. During cooler months, tests were scheduled in the warmer afternoons, whereas during very warm months, tests were done in the cooler early morning hours.

The three-hour means of KD and bite data for weekly tests were computed but not analyzed, because only one replicate test of each treatment was made each week. Means of these weekly data were computed to provide a monthly view of treatment effect. Weekly bite data were calculated to percent protection by the following formula: the percentage of protection equals the percentage of mosquitoes biting in the control tent minus the percentage of mosquitoes biting in a treated tent divided by the percentage of mosquitoes biting in the control tent.

RESULTS

Presented in the following Table 1 are means of the monthly data shown as percent KD/biting during weekly exposures of *Ae. aegypti* to treated tents. Mean KD in the DMP-treated tent for the year was greater (2.7%) than in the untreated control (0.9%). However, the mean KD effect of DMP was never as high as that of permethrin (58.6%). Mean monthly KD in the control tent was rather consistent (0.87% plus or minus 0.78%) for the year. This was also true for the DMP tent, except for the first 12 weeks when KD averaged 8.5% plus or minus 10.4%.

Mean biting in the permethrin-treated tent for the year was 11.9%, in the DMP-treated tent 43.8% and in the control tent 58.6%. With permethrin, biting averaged less than 1% for the first six months, 8.5% for the next three months and 33.8% for the last three months. Biting in the DMP-treated tent rose from 21.3 to more than 40% after the 11th week and continued at this, or a somewhat higher level, for the duration of the study.

Figure 3:
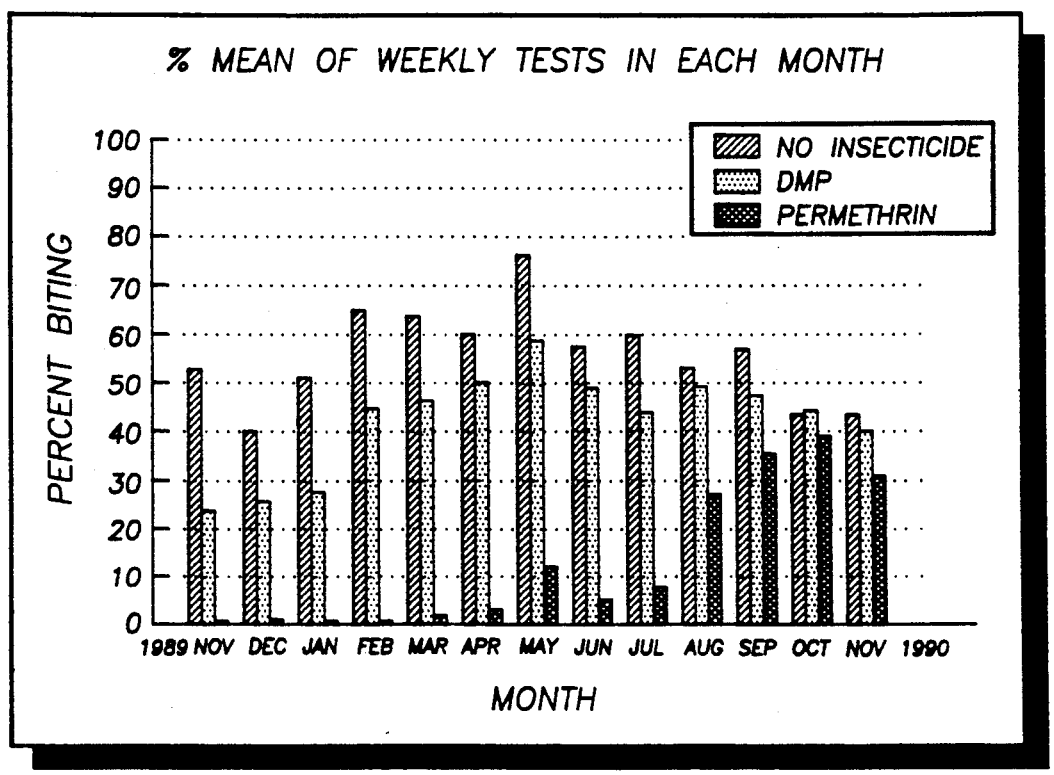
FIG. 3 is a chart illustrating the percentage of mosquito bites each month during a year long test of two tents treated with different insecticides and an untreated control tent.
Figure 4:
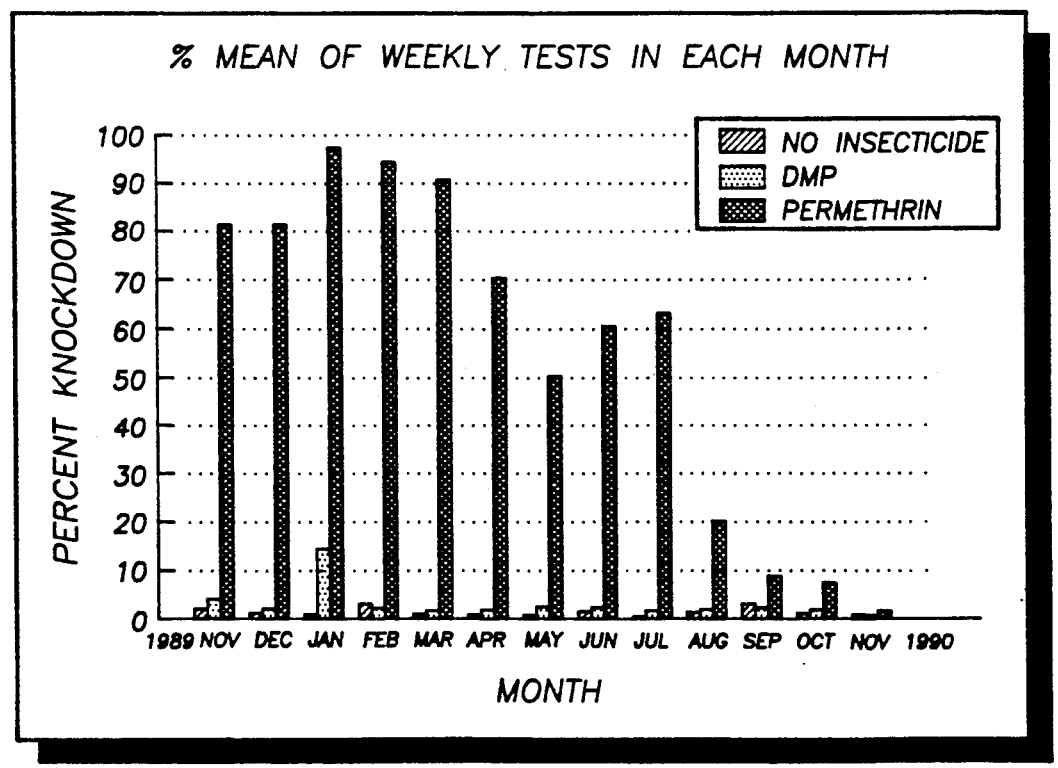
FIG. 4 is a chart illustrating the percentage of mosquitoes killed each month during the same year long test of two tents treated with different insecticides and an untreated control tent.

A comparison of th permethrin, DMP, and untreated control data are presented in FIGS. 3 and 4. Biting was reduced in the DMP-treated tent, and there was a KD effect with an overall average of 19.8% fewer bites and 2.7% more KD than in the control tent during the first 30 weeks.

TABLE 1

Monthly mean percentages of *Aedes aegypti* mosquitoes biting or knocked down after weekly three hour exposures to three different tent fabrics, one treated* on its inner surface only with permethrin, one treated on the inner and outer surfaces with dimethyl phthalate (DMP), and the third tent fabric not treated with any insecticide.

| Month Number | Percent Knockdown | | | Percent Biting | | |
|---|---|---|---|---|---|---|
| | Per-methrin | DMP | Un-treated | Per-methrin | DMP | Un-treated |
| 1 & 2** | 81.9 | 2.5 | 0.8 | 0.4 | 24.2 | 47.6 |
| 3 | 99.0 | 14.4 | 0.3 | 0.0 | 26.1 | 52.3 |
| 4 | 96.8 | 2.1 | 2.6 | 0.5 | 43.6 | 67.4 |
| 5 | 94.4 | 1.1 | 0.5 | 1.5 | 46.9 | 66.2 |
| 6 | 71.3 | 1.4 | 0.5 | 2.1 | 50.5 | 61.5 |
| 7 | 48.6 | 1.7 | 0.6 | 13.4 | 57.3 | 75.9 |
| 8 | 56.9 | 1.5 | 0.9 | 4.9 | 49.6 | 56.6 |
| 9 | 58.9 | 1.1 | 0.2 | 7.1 | 42.8 | 58.8 |
| 10 | 24.3 | 1.4 | 0.9 | 27.2 | 48.4 | 51.7 |
| 11 | 7.2 | 1.5 | 2.1 | 34.9 | 46.9 | 54.3 |
| 12 | 5.0 | 0.7 | 0.2 | 39.3 | 45.4 | 45.5 |
| Year avg. | 58.6 | 2.7 | 0.9 | 11.9 | 43.8 | 57.9 |

*Treatment was 0.075 ounces per square yard of permethrin active ingredient.
**Data for weeks 1, 2, 3 and 8 are absent because no tests were run. Thus, data for weeks 4, 5, 6 and 7 were combined and analyzed for this two month period.

Figure 5:
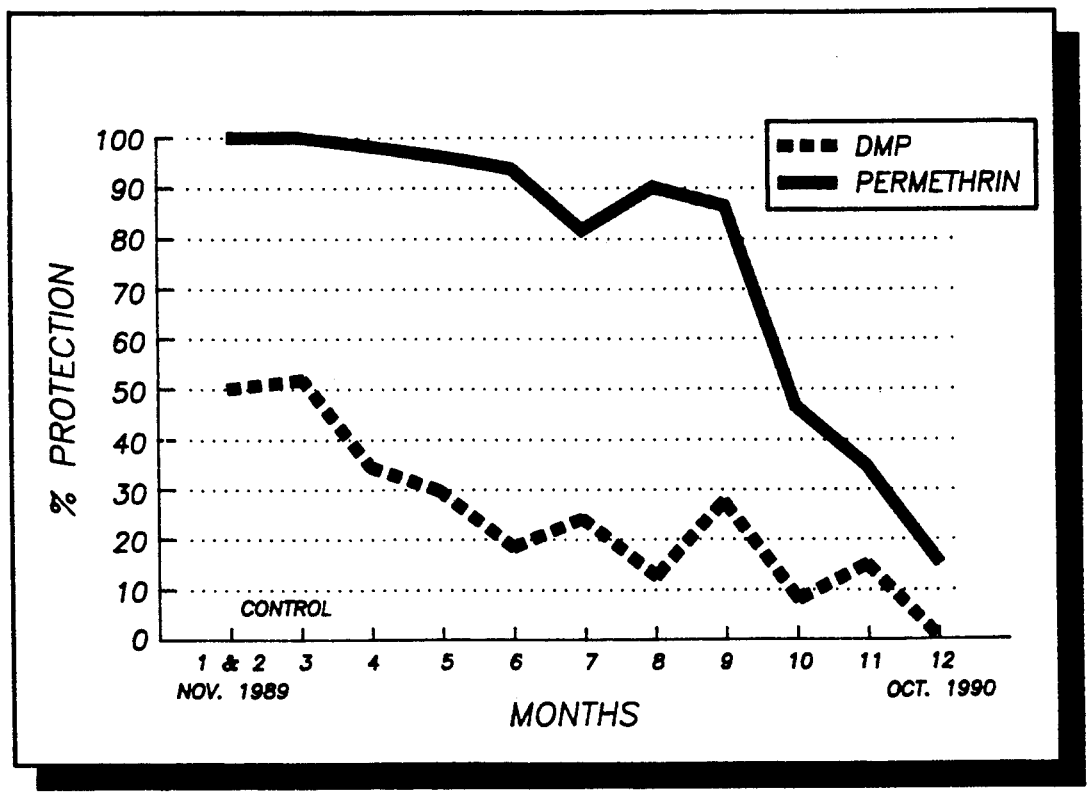
FIG. 5 is a graphic illustration of the effects of ageing and weathering on tent fabrics treated with different insecticides and on an untreated control tent, as indicated by protection from mosquito bites.

The foregoing data is graphically illustrated in FIGS. 3, 4, and 5.

The average monthly percentage of biting and Kd in the permethrin-treated tent was clearly superior to that in the DMP-treated tent and the tent treated without an insecticide. In the permethrin-treated tent from November to July, percent biting was sell below 10% with the exception of May, which was 31.4%. This would provide the user with more than 96% protection from mosquito bites for nine months. Average Knock Down was only about 88% for six months (November through April), indicating that although the permethrin treatment provided less than 100% KD, mosquitoes were affected enough by the toxicant for it to strongly inhibit biting for nine months.

The long effective life (nine (9) months) is attributed to the protection provided by the wax and plasticizer covering the permethrin, and to the fabric layer of the tent acting as a barrier that inhibits migration of the pyrethrin to the outer surface of the fabric and consequently inhibits exposure of the permethrin to degrading environmental elements.

DISCUSSION

From November to July, mean numbers of mosquitoes biting in the permethrin-treated tent were less than 4% of those released. High levels (more than 96%) of overall protection from bites of *Ae. aegypti* (FIG. 1) existed for up to nine months.

Protection may be longer with intermittent rather than constant exposure of the treatment to weathering. Average KD was about 88% for six months (November through April). Thus, even when the permethrin treatment produced less KD as the treatment aged and weathered, there was sufficient residual toxicity to effectively reduce biting for up to nine months. Variables such as temperature, humidity, solar radiation, precipitation and wind may account for some weekly differences in test data. For example, with permethrin there was a 14% drop in protection from bites the seventh month (FIG. 1), a time when solar radiation was the highest recorded. Unexpectedly, the DMP treatment caused some KD, indicating it had insecticidal activity. However, it is obvious that permethrin was superior to DMP in KD, protection from bites, and duration of persistence.

There is thus provided a tent fabric which is coated to be permanently water repellent and flame retardant, and insect repellent for as long as nine months.

Although specific terms have been employed in describing the invention, they have been used in a descriptive and generic sense only and not for the purpose of limitation. It is intended that the scope of the patent be determined from the following claims to invention, considered with the specification and drawings and with the prior art.

We claim:

1. A coated tent fabric having a fabric substrate with a coated outer surface normally exposed to degrading elements of the atmosphere and a coated inner surface normally shielded by the fabric substrate from the degrading elements of the atmosphere, the coatings on the outer and inner surfaces of said fabric substrate each containing a polymeric binder, flame retardant chemicals and water repellent chemicals, wherein the improvement comprises the addition of permethrin as an insect repellent to the coating on the inner surface of the fabric substrate, whereby the fabric substrate acts as a barrier that inhibits migration of the permethrin to the outer surface of the fabric and consequently inhibits exposure of the permethrin to the degrading elements of the atmosphere, thereby increasing the length of time the permethrin is an effective insect repellent.

2. The invention of claim 1 wherein the coating on the inner surface of the fabric substrate also contains means for mobilizing the permethrin to the extent of keeping enough permethrin on the inner surface of the fabric substrate to be an effective insect repellent for at least nine months.

3. The invention of claim 2 wherein the permethrin is applied to only the coating on the inner surface of the fabric substrate.

4. The invention of claim 2 wherein the means for mobilizing the permethrin is a plasticizer.

5. The invention of claim 4 wherein the plasticizer is zirconium wax.

* * * * *